(12) United States Patent
Herguijuela et al.

(10) Patent No.: US 7,858,813 B2
(45) Date of Patent: Dec. 28, 2010

(54) PROCESS FOR THE RECTIFICATION OF MIXTURES OF HIGH-BOILING AIR-AND/OR TEMPERATURE-SENSITIVE USEFUL PRODUCTS

(75) Inventors: Juan Herguijuela, Auggen (DE);
Werner Pietzonka, Therwil (CH);
Angela Wildermann, Bad Säckingen (DE); Thomas Wolf, Rheinfelden (DE)

(73) Assignee: DSM IP Assets B.V., Heerlen (NL)

( * ) Notice: Subject to any disclaimer, the term of this patent is extended or adjusted under 35 U.S.C. 154(b) by 332 days.

(21) Appl. No.: 11/660,103

(22) PCT Filed: Aug. 13, 2005

(86) PCT No.: PCT/EP2005/008822

§ 371 (c)(1),
(2), (4) Date: Dec. 4, 2007

(87) PCT Pub. No.: WO2006/018256

PCT Pub. Date: Feb. 23, 2006

(65) Prior Publication Data

US 2008/0194846 A1    Aug. 14, 2008

(30) Foreign Application Priority Data

Aug. 19, 2004    (CH) .................................. 01365/04

(51) Int. Cl.
C07D 311/00    (2006.01)
B01D 3/14    (2006.01)
(52) U.S. Cl. ...................................... 549/413; 202/161
(58) Field of Classification Search .................. 549/413; 202/161
See application file for complete search history.

(56) References Cited

U.S. PATENT DOCUMENTS

| 5,582,692 | A | 12/1996 | Baird |
| 6,111,117 | A * | 8/2000 | Hartmann et al. ............ 549/413 |
| 6,221,873 | B1 | 4/2001 | Havlicek et al. |
| 6,518,439 | B1 | 2/2003 | Dhainaut et al. |
| 6,531,479 | B2 | 3/2003 | Wang |
| 6,569,833 | B1 | 5/2003 | Fahraeus |
| 6,699,854 | B2 | 3/2004 | Wang |
| 6,703,395 | B2 | 3/2004 | Havlicek |
| 7,041,701 | B2 | 5/2006 | Hajduch et al. |

FOREIGN PATENT DOCUMENTS

| DE | 27 43 920 A | 3/1978 |
| DE | 42 08 477 A1 | 9/1993 |
| DE | 197 33 503 A | 2/1999 |
| GB | 867166 | 5/1961 |
| WO | WO 97/02880 * | 1/1997 |
| WO | WO-02/22601 A1 | 3/2002 |
| WO | WO 02/42286 A1 | 5/2002 |
| WO | WO-03/002565 A1 | 1/2003 |
| WO | WO 03/011850 A1 | 2/2003 |
| WO | WO-2004/018473 A2 | 3/2004 |

OTHER PUBLICATIONS

El-Gaby, Mohamed S.A. et al., "Preparation of Some Novel 3,5-Diaminopyrazole, Pyrazolo-[1,5-a] (1,3,5}Triazine and Pyrazolo(1,5-a)-Pyrimidine Derivatives Containing Sulfonamido Moieties as Antimicrobial Agents," *Acta Chim. Slov.*, vol. 49:159-171 (2002).

Elgemeie, Gatal H. et al., "Preparation and characterization of novel methylsulfanyl-pyrazolopyrimidine and methylsulfanyl-pyrazolotriazine azo dyes," *Pigment and Resin Technology*, vol. 31(5):297-309 (2002).

Fathy, N.M. et al., "Behaviour of 3,5-Diaminopyrazoles Towards Activated Double Bond Systems: Novel Synthesis of Pyrazolo [1,5-a] Pyrimidines," *Egypt. J. Pharma. Sci.*, vol. 33(1-2):1-9 (1992).

Shvekhgeimer, M.-G A., Synthesis of Novel 3,5-Diamino-4-(2-Cyano-Arylazo)Pyrazoles, *Chemistry of Heterocyclic Compounds*, vol. 37(3):370-371 (2001).

Wiedermannová, Iveta et al., "Oxo Derivatives of Quinoxaline VI Synthesis of Some Arylhydrazones of 6,7-Disubstituted-1,2-Dihydro-Quinoxaline-3-Carbaldehyde," *Acta Universitatis Palackianae Olomucensis, Facultas Return Naturalium*, vol. 41:59-63 (2002).

Zhu, Youyu et al., "Study on the color reaction of palladium with 4-(6'-methylbenzothiazolyl-2'-azo)-3,5-diaminopyrazole and its application," *Huaxue Shiji*, vol. 15(5):274-276 (1993).

Written Opinion for Application No. PCT/GB2005/003383, dated Mar. 6, 2007.

* cited by examiner

*Primary Examiner*—Nizal S Chandrakumar
(74) *Attorney, Agent, or Firm*—Nixon & Vanderhye P.C.

(57) ABSTRACT

According to the invention, a process for the rectification of mixtures of high-boiling air- and/or temperature-sensitive substances which require a high separation efficiency is proposed, in particular a process for the working-up of a VE- or VEA-containing product stream. The process is characterized in particular in that, in a first purification stage, low-boiling products and unspecified isomers of the useful product are separated from the product stream virtually without loss of useful product and that, in a second purification stage, the useful product is removed in a stream having a purity of >97% by weight and a further stream having a purity of >92% by weight. A preferred embodiment of the process serves for working up VEA, in which the loss of useful product in the first purification stage is less than 5%, based on that amount of VEA in the feed which is added to the purification stage per unit time. Furthermore, the first purification stage may comprise a rectification column (1), from the top (Ia) of which the low-boiling products and the unspecified isomers of VEA are taken off, a stream containing the useful product in purified form being taken off at the side (15) and/or at the bottom (Ib) of the column (1).

9 Claims, 3 Drawing Sheets

Figure 1:
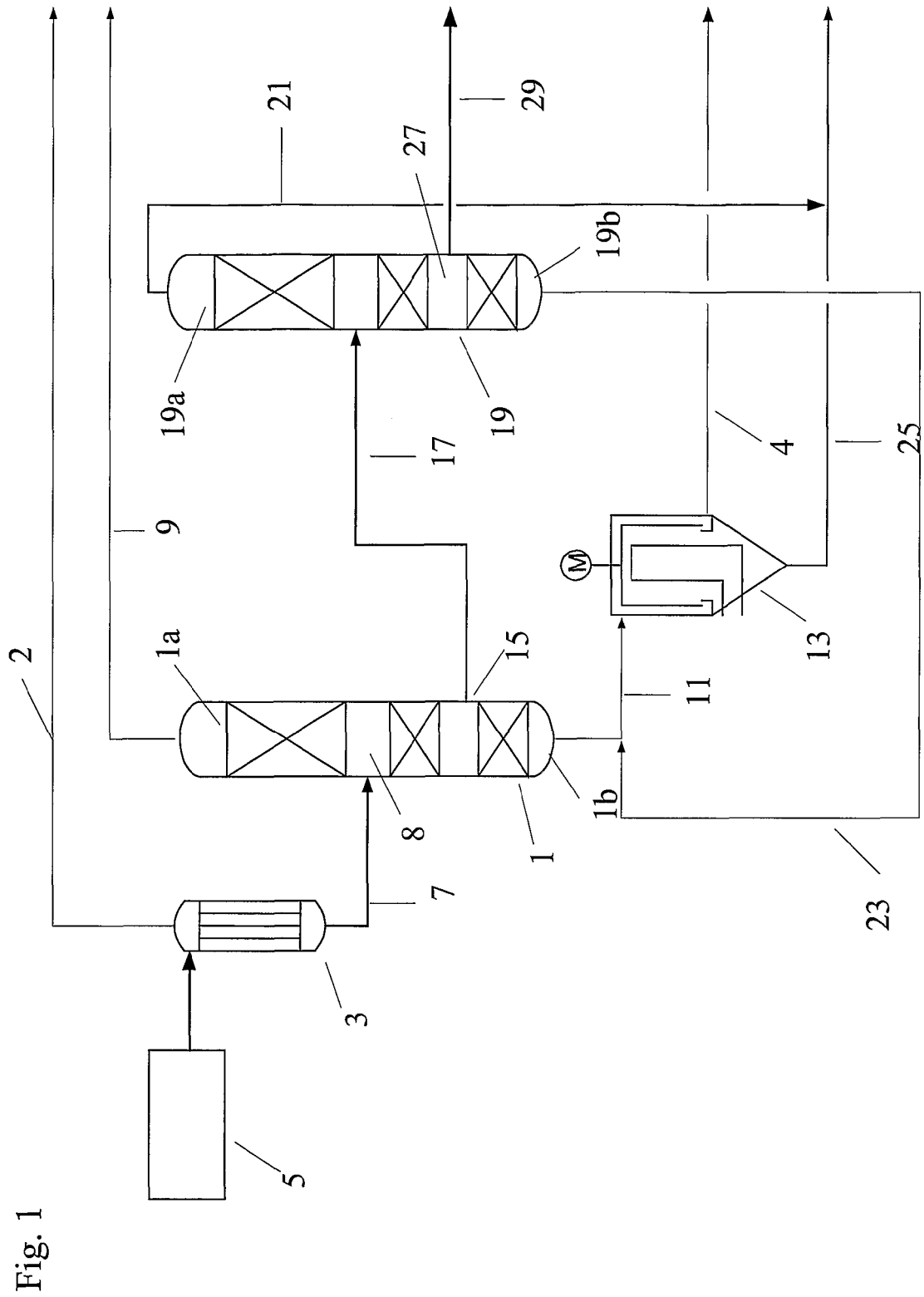

PROCESS FOR THE RECTIFICATION OF MIXTURES OF HIGH-BOILING AIR-AND/OR TEMPERATURE-SENSITIVE USEFUL PRODUCTS

This application is the US national phase of international application PCT/EP2005/008822 filed 13 Aug. 2005 which designated the U.S. and claims benefit of CH 01365/04, dated 19 Aug. 2004, the entire content of which is hereby incorporated by reference.

The invention relates to a process for the rectification of mixtures of high-boiling air- and/or temperature-sensitive substances, in particular the rectification of tocopherol acetate—also referred to as vitamin E acetate (VEA)—for separating lower-boiling and higher-boiling impurities from the useful product.

The VEA obtained by esterification of vitamin E with acetic anhydride, also referred to below as crude VEA, can be freed from the substantial residues of acetic acid and acetic anhydride and other impurities, for example, by multistage distillation steps in falling-film evaporators, thin-film evaporators, etc. Usually, such a reaction mixture then contains about 94% by weight of VEA, 1-2% by weight of low-boiling substances (chiefly phytadienes), about 2-3% by weight of unspecified isomers of the useful product (VEA) and 1-2% by weight of high-boiling secondary components.

In the industrial purification of a VEA-containing product stream, for example, cascades of short-path evaporators are used. As complete as possible a separation of the low-boiling substances from the product stream flowing to the cascade of short-path evaporators is decisive for the dimensioning and the operation of the short-path evaporators and the vacuum system at the required, very low pressures. A thin-film evaporator usually operated at about 1 mbar and intended for removing the low boilers is therefore connected upstream of the cascade of short-path evaporators. The vapour stream produced in the thin-film evaporator contains substantially phytadienes, vitamin E acetate and residues of acetic acid and acetic anhydride and is virtually completely condensed in a downstream condenser system. Owing to the high content of low boilers, the condensate obtained cannot be further used and is discarded. Because of the position of the phase equilibrium, the proportion of VEA in this vapour stream is about 13% by weight and the loss of VEA is about 2.7%, based on the inflowing amount of VEA. A low boiler fraction of, usually, about 2% by weight remains in the useful product (bottom product of the thin-film evaporator). The bottom product of the thin-film evaporator is fed to the cascade of short-path evaporators, in which the VEA is further enriched by repeated evaporation and condensation.

The process described above and intended for obtaining VEA has the following disadvantages. As already mentioned, a part of the useful product (VEA) passes out of the thin-film evaporator via the gas phase to the downstream condenser system and is finally lost. Furthermore, only parts of the low boilers are separated off in the thin-film evaporator, which is per se a relatively complicated and expensive apparatus, and the rest remains in the useful product and has to be separated off later on by a complicated procedure. At the same time, owing to the incomplete separation of the main product from the byproducts in the respective purification steps, this process also includes recycled streams which have to be fed back to the process by a relatively complicated procedure.

Since VEA is being used to an increasing extent for human nutrition or prophylaxis in healthcare, the purity of this product has to meet increasingly high requirements. The VEA quality required for these intended uses, also referred to below as "pharma grade" (PG) quality, is defined as follows:
Purity$\geq$97.5% by weight
Colourless to slightly greenish yellow VEA obtained from the process described above has a purity of <97% by weight. With a purity of >92% by weight, it fulfils the condition which is set for the so-called "technical grade" (TG) quality of the useful product but not the requirements of a PG quality. For use as a food additive or for medical applications, it must therefore be subjected to further purification steps.

It is known that, in the working up of product mixtures by distillation, the best results are generally obtained when so-called countercurrent distillation (also referred to as rectification) is used, i.e. a special distillation process with countercurrent flow of descending reflux and ascending vapour in rectification columns. It is usual to use columns in which the mixture to be separated is introduced in the middle part of the column, the vapour becomes enriched with more readily volatile components on its way through the column from bottom to top and the reflux becomes enriched with more sparingly volatile components from top to bottom. The transport of material and heat is intensified by elements installed in the column, such as column trays, random packings or structured packings, which ensure a sufficient contact time of the phases and a sufficiently large phase boundary.

It is furthermore known that, for the separation of high-boiling, temperature-sensitive mixtures of substances which require a high separation efficiency, which also includes the mixture present here (crude VEA), it is preferable to use rectification columns which have packings composed systematically in a regular geometry and having defined passage regions for countercurrent phases. This is the case in particular because, compared with random packings, regularly structured packings are distinguished by a higher load capacity and a better separation effect, have a smaller specific pressure drop and require a smaller volume of packings and therefore also permit a smaller mass and heat transfer height. Structured packings are therefore used in all vacuum rectifications, in which, owing to the temperature sensitivity of the mixture to be separated, a limitation of the column pressure drop is particularly important. Column packings known for this intended use are metal fabric packings of the BX and CY type from Sulzer, expanded metal packings of the Optiflow or Mellapak type and Rhombopak type from Sulzer and Kühni, respectively, and similarly effective metal fabric packings from other companies, such as Montz GmbH.

The rectification of a VEA-containing mixture is disclosed, for example, in WO 97/02880. However, the rectification generally advantageous for the purification of products on an industrial scale presents major problems in this case owing to the high boiling point of VEA and its decomposability at higher temperatures. Substantially distillation under high vacuum or even molecular distillations are therefore carried out in order to be able to distil VEA at as low temperatures as possible.

In spite of the use of the high vacuum, in general only purities of 97.3% (DE-A 27 43 920), 98% (DE-A 42 08 477 and JP-B-58 011 869), 98.5% (U.S. Pat. No. 3,459,773) or 98.5 to 99% (DE-A 21 60 103) are achieved according to the prior art. Purities above 99% were achieved only by molecular distillation, namely purities of 99.3% according to JP-A 51/14671 and 99.5% according to JP-A-62/226976, it being necessary to point out that, on investigation by the more precise methods of analysis used today and with the use of purer comparative substances, presumably lower purity values would be achieved. In addition, the distillation yields achievable in this manner are in each case very low, and both the capital costs and the ongoing operating costs of such plants are therefore very high owing to the extreme complexity.

It is the object of the invention to provide a process for the rectification of mixtures of high-boiling air- and/or temperature-sensitive useful products, but in particular a process for working up a VEA-containing product stream, which process does not have the above-mentioned disadvantages and which permits an economical method, which is simple in terms of process engineering, for separating off the useful product in high purity and high yield. In addition, the process should also permit the use of separation apparatuses which are simple in terms of process engineering and should make it possible to prepare two end products in different and optionally variable proportions, which end products differ in their purity. It is also considered advantageous to develop a process without recycling for treatment of the products under milder conditions.

This object is achieved by a process having the features of Patent claim 1.

Advantageous embodiments of the invention form the subject of the dependent claims.

Claim 1 proposes a process for the rectification of mixtures of high-boiling air- and/or temperature-sensitive substances which require high separation efficiency, in particular a process for working up a VE- or VEA-containing product stream, which is characterized in that, in a first purification stage, low-boiling products are separated from the product stream virtually without loss of useful product, and unspecified isomers of the useful product are taken off, and that, in a second purification stage, the useful product is removed in one stream with a purity of >97% by weight and in a further stream with a purity of >92% by weight.

According to the invention, a completely novel concept for the purification of high-boiling air- and/or temperature-sensitive substances, for example VEA, was developed. Only pure waste streams (low boilers, i.e. streams of low-boiling substances/streams comprising unspecified isomers of the useful product/streams of high-boiling byproducts, in each case having a very low VEA content) and pure product streams form. Thus, no streams which require further working-up are produced, which also permits the elimination of disadvantageous recycling.

A preferred embodiment of the process serves for working up VEA, in which the loss of the useful product in the first purification stage is less than 5%, based on the amount of VEA in the feed which is added to the purification stage per unit time. In this particular case, the first purification stage may comprise a rectification column, from the top of which the low-boiling products and the unspecified isomers of VEA are taken off, a stream containing the useful product in purified form being taken off at the side and/or at the bottom of the column.

The side take-off or the bottom take-off of the first rectification column can then be fed, in the second purification stage, to a second rectification column, from which VEA is then removed either as a bottom take-off having a purity of >97% by weight and as a top take-off having a purity of >92% by weight, or
as a side take-off having a purity of >97% by weight and as a mixture consisting of top take-off and distillate of the bottom take-off having a purity of >92% by weight.

According to the invention, the two rectification columns have structured packings having a ratio of separation efficiency to pressure drop of, preferably, >15 theoretical plates per mbar of pressure drop (basis: F factor=1 $Pa^{0.5}$, column diameter 1 meter, test mixture cis-/trans-decalin). A particularly suitable structured packing is the OPTIFLOW packing from Sulzer AG. According to the invention, at least the side take-off is effected at the second column by partial condensation in a manner such that the product to be separated off leaves the column as condensate and not as a product stream in vapour form. For this purpose, the columns incorporate important design details which are important for the condensation process.

The advantages of the preferred processes according to the invention are the following:

A sharp separation in one column is achieved. Usually, a plurality of columns is required for this purpose.
In particular the first column has a high separation efficiency in combination with a small pressure drop.
The losses of products are very small.
The purity of the pharma grade product is very high, with a VEA content of $\geq$97% by weight.
The process is very flexible with regard to the amounts of product to be produced in PG or TG quality.

In a further preferred embodiment of the invention, before crude VEA is fed to the first column, the product stream is passed for degassing into a falling-film evaporator in which in particular the low-boiling substances, such as, for example, solvent residues, and any remaining traces of acetic acid and acetic anhydride are removed. The falling-film evaporator can also be designed thereby in such a way that it also serves for reducing the total chlorine content in the crude VEA, in order thereby to avoid any disadvantageous corrosion in the following stages. In the first column, the remaining low-boiling substances and the unspecified isomers of the useful product are then separated off at the top, and the VEA is removed as a side take-off in vapour form with a content of >96%. For the preparation of the "pharma grade" quality, the side take-off stream of the first column is rectified again in the second column. According to the invention, the "pharma grade" quality is taken off as a side take-off. The bottom product from the first column is squeezed out in a short-path evaporator and gives the VEA-TG as a distillate together with the top product of the second column.

The invention is explained in more detail below with reference to the drawing.

Figure 2:
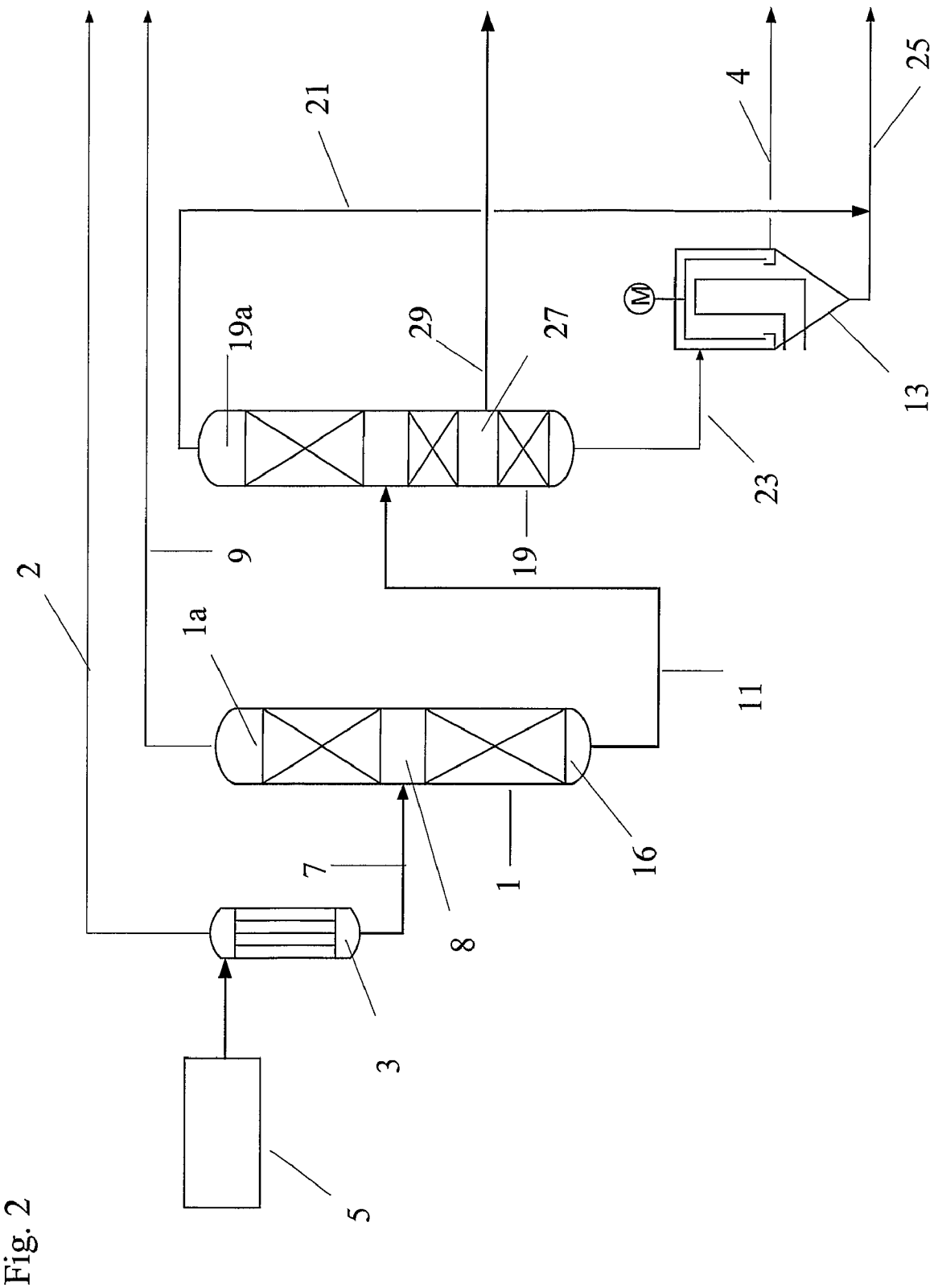
Figure 3:
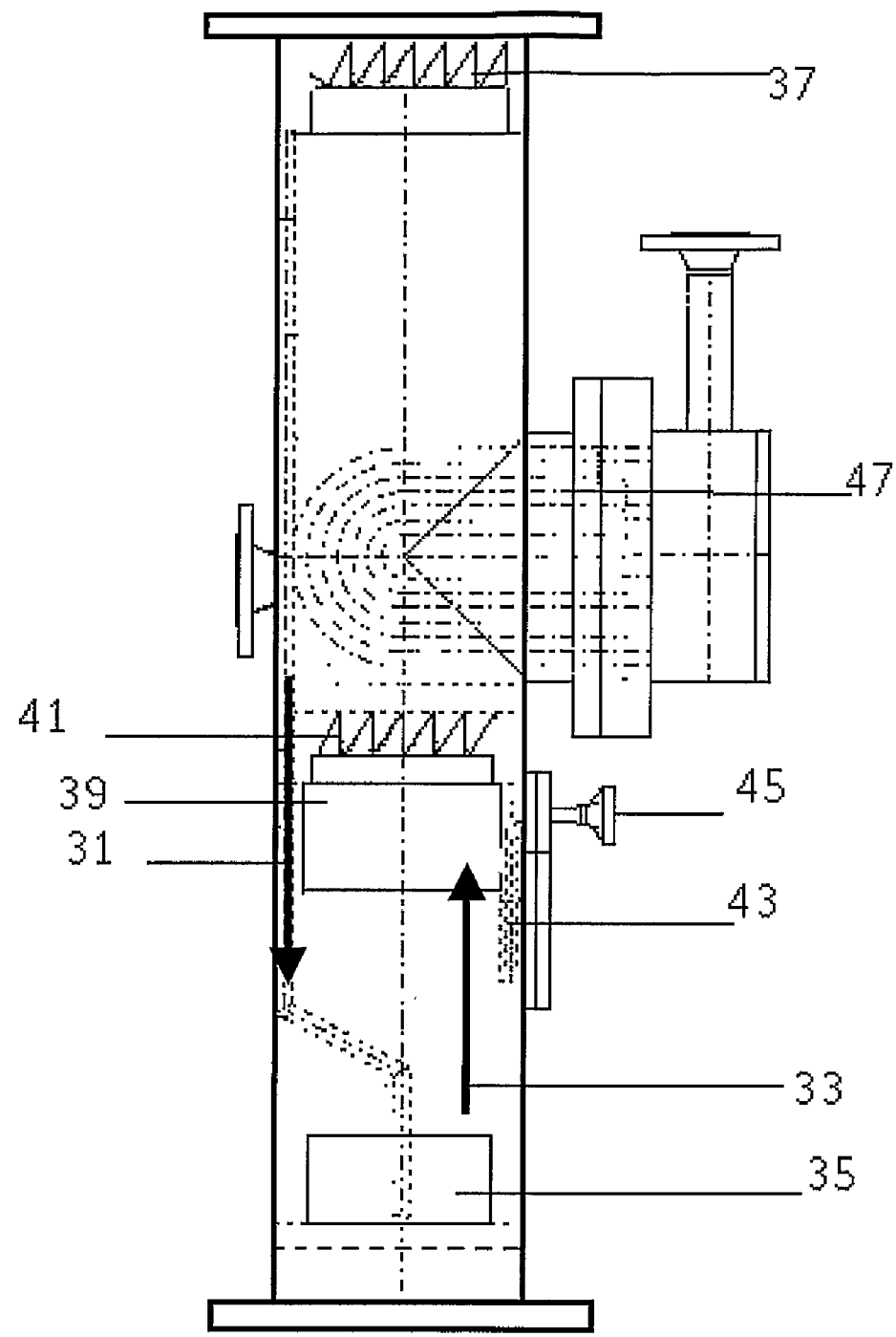

In the drawing,

FIG. 1 shows a schematic diagram of the process according to the invention, designed for working up VEA, FIG. 2 shows an alternative method of carrying out the process according to FIG. 1 and FIG. 3 shows a side take-off point as provided according to the invention in the second and, if required, first rectification column.

The procedure shown in FIG. 1 for the preparation of VEA has the following organization. The crude VEA originating from the acetylation stage 5 (conversion of vitamin E into VEA, including separating off the main portion of acetic acid and acetic anhydride) is fed to the degasser 3 (falling-film evaporator). There, the remaining low-boiling components, such as, for example, acetic acid or acetic anhydride, are removed via the line 2. The degassed crude VEA obtained at the bottom of the degasser 3 is added as feed approximately in the middle of the rectification column 1. At the top 1a of the column 1, lower-boiling components and unspecified isomers of the useful product are removed via the line 9 virtually without loss of useful product. The bottom take-off obtained at the bottom 1b of the column 1 is fed via the line 11 to the short-path evaporator 13. The loss of the useful product VEA via the top take-off of the first rectification column 1 is <5%, preferably <1% and ideally <0.5%, based on that amount of VEA in the feed which is added to the column per unit time.

The column 1 furthermore has a side take-off 15 which is present below the column feed. The side take-off of the column 1 is connected via the line 17 to a second rectification column 19, here too the feed being arranged approximately in the middle of the column. The bottom take-off formed at the bottom 19b of the column 19 is fed to the short-path evaporator 13 via the line 23 together with the bottom take-off of the column 1 via the line 11. In the short-path distillation, a residue stream 4 and a distillate stream 25 are obtained. The distillate stream 25 is mixed with the top take-off obtained at the top 19a of the column 19.

According to the invention, the column 19 also has a side take-off 27, as described in more detail below. Furthermore, both columns 1 and 19 each have a condenser arranged in the top 1a and 19a, respectively, and an evaporator provided in the bottom 1b and 19b, respectively. These components which as such are conventional and customary for rectification columns are generally known to a person skilled in the art and are therefore neither described in detail nor shown in the drawing. According to the invention, the two rectification columns are packed with structured packings, the ratio of separation efficiency to pressure drop of which is greater than 15 theoretical plates per mbar pressure drop (basis: F factor 1 $Pa^{0.5}$, column diameter 1 meter, test mixture cis-/trans-decalin). The principle of the process according to FIG. 1 is distinguished by the fact that the remaining traces of low-boiling components, such as, for example, acetic acid, acetic anhydride or solvent residues from the product stream arriving from the acetylation, are removed from the crude VEA in the upstream degasser 3 and are transported away via the line 2.

In the first column 1, the remaining lower-boiling components and also the unspecified isomers of the useful product are then separated off at the top 1a, and a VEA having a content of >96% by weight is removed at the side take-off point 15 by partial condensation.

According to the invention, the column 1 is operated as follows:

The side take-off comprises about 75% by weight, based on the feed stream added, this having as high a VEA content as possible with a small amount of unspecified isomers of the useful product and high-boiling components.

The top take-off comprises about 2 to 5% by weight, based on the feed stream.

The top condenser arranged in the top 105a virtually completely condenses the incoming vapour stream to give reflux and top take-off.

The pressure at the top of the column is preferably about 0.5 to 1 mbar and is as far as possible kept constant, and the column temperatures are between 190 and 280° C., depending on the loading of the column.

On maintaining these guide parameters, and depending on the established reflux ratio of column 1, the latter can be operated so that the VEA content in the side take-off is well above 95% by weight and that in the top take-off is substantially below 20% by weight.

The side take-off of the first column 1 is fed via the line 17 to the second column 19 in order to prepare VEA-PG. The take-off of this quality is in turn effected as a side take-off by partial condensation at position 27 and is removed from the plant via product line 29.

The bottom product emerging from the bottom 1b of the first column 1 is squeezed out together with the bottom product of the second column 19 in the short-path evaporator 13 and gives a distillate which, together with the product of the second column 19, emerging from the top 19a of the second column 19, forms the VEA-TG.

In the alternative method of carrying out the process for the preparation or purification of the VEA products, shown in FIG. 2, there is no side take-off from the first column 1. Instead, the bottom product of the column 1 is transported via the product stream line 11 directly and completely to the second column 19. As a result of this, the feed to the short-path evaporator consists only of the bottom take-off of the column 19, and in this case the VEA-TG is formed only from the mixture of the top product and the distillate of the bottom product of the second column 19.

The side take-off by partial condensation in the columns 19 and/or 1 is decisive for carrying out the preferred process according to the invention. This side take-off will therefore be explained in more detail before the purification of VEA is described in more detail with reference to two specific examples.

In the section of the two rectification columns 1 and 19 according to the invention, shown in FIG. 3, the countercurrent flow is characterized by the descending reflux-stream 31 and ascending vapour stream 33 in the rectification column, in the region of the side take-off point the vapour flowing through the packings and separating elements of the side take-off from bottom to top, and the reflux flowing inside a guide pipe from top to bottom.

A distributor 35 which redistributes the reflux from the collector bed 37 above the side take-off is present in the lower region of the side take-off point. In order to avoid contamination of the (vapour) side take-off with liquid, a half layer of Mellapak 250X is installed as a splash guard 39. Directly above this layer 39, the collector 41 for the side take-off is provided. The collector 41 empties, for example, into a trap 43 which opens into an outlet 45 intended for removal of the vapour condensate to be separated off. Above the collector 41 there follows a side take-off partial condenser 47 which, for example, is in the form of a U-tube bundle heat exchanger and serves for producing the vapour condensate. A total take-off collector 37, which transports the reflux—as already mentioned—from the upper part of the side take-off point past the partial condenser 47 into the lower distributor 35 is preferably present as the uppermost element. It is advantageous that the collector 37 carries out a total take-off so that the side take-off is not contaminated by the reflux or adversely affects the colour of the side take-off.

According to the invention, the side take-off is effected by partial condensation of the vapour phase ascending in the column. This has the advantage that a vapour condensate, i.e. not a product stream in vapour form, is taken off as a side take-off, with the result that the pressure drop caused by the take-off and owing to the smaller volume streams of the liquids can be significantly reduced. Since the take-off involves a partial condensation, an additional purification stage is furthermore obtained, which also proves to be particularly advantageous.

It should be pointed out here that the process described with reference to FIGS. 1 and 2 represents only one working example of the invention and that in particular the design of the plant which serves for carrying out the process can vary in different respects within the scope of protection defined by claim 1. Thus, the process according to the invention and the partial side take-off can also be used for the purification of vitamin E (VE) and of course also for the working-up or purification of other substances which, like VE and VEA, are high-boiling and temperature-sensitive and are usually purified by means of rectification columns.

The processes described above with reference to FIGS. 1 and 2 will now be described in detail by means of two specific examples.

EXAMPLE 1

With Reference to FIG. 1

Synthetically prepared crude VEA having a content of about 90 to 92% of VEA, about 2-3% of low-boiling components (chiefly phytadienes), about 2-3% of unspecified isomers of the useful product (VEA) and about 3-4% of high-boiling components is degassed in a falling-film evaporator at 185° C. and about 3 mbar. The degassed crude VEA is fed in at a temperature of between 180 and 250° C. approximately in the middle of the rectification column 1 with a packing height of 6 to 8 m of the Sulzer Optiflow C36 type. The pressure at the top of the column is about 0.5 to 1 mbar. At the top of the column 1, about 4% by mass of the feed-stream is removed as a top take-off with a content of about 3% of VEA. The column 1 is operated at a reflux ratio of about 10 to 20. The side take-off point is about 2 to 3 m of packing height below the feed inflow point. About 75% of the feed stream having a VEA content of about 96-97% are removed at the side take-off. The desired flow rate is set by regulation of the partial condenser forward flow temperature. The product obtained at the bottom of the column 1 at a temperature of 260 to 270° C. still contains about 80-82% of VEA.

The side take-off of the column 1 having a VEA content of about 96 to 97% is then added at a temperature between 180 and 250° C. as feed approximately in the middle of the rectification column 19 having a packing height of 6 to 8 m of the Sulzer Optiflow C36 type. The pressure at the top of the column 19 is about 0.5 to 1 mbar. At the top of the column 19, about 5 to 15% by mass of the feed stream are removed as a top take-off having a content of about 92 to 95% of VEA. The column 19 is operated at a reflux ratio of about 15 to 30. The side take-off point is about 2 to 3 m of packing height below the feed inflow point. At the side take-off, depending on the desired amount of PG, between 50 and 78% (the latter corresponds to 60% of the VEA used in the form of PG) of the feed stream with a VEA content of more than 97% are removed. The desired flow rate is established by regulation of the partial condenser forward flow temperature. The product obtained at the bottom of the column 19 at a temperature of 260 to 270° C. still contains about 90-95% of VEA, depending on the split ratio set.

The bottom products of the columns 1 and 19 are now fed to the short-path evaporator 13, which is operated at a pressure of about 0.1 to 0.2 mbar. The residue still contains about 2-5% of VEA, while the VEA content in the distillate is about 92%. The distillate is mixed together with the top take-off of the column 19 to give VEA TG.

EXAMPLE 2

With Reference to FIG. 2

Synthetically prepared crude VEA having a content of about 90 to 92% of VEA, about 2-3% of low-boiling components (chiefly phytadienes), about 2-3% of unspecified isomers of the useful product (VEA) and about 3-4% of high-boiling components is degassed in a falling-film evaporator at 185° C. and about 3 mbar. The degassed crude VEA is fed in at a temperature of between 180 and 250° C. approximately in the middle of the rectification column 1 with a packing height of 6 to 8 m of the Sulzer Optiflow C36 type. The pressure at the top of the column is about 0.5 to 1 mbar. At the top of the column 1, about 4% by mass of the feed stream is removed as a top take-off with a content of about 3% of VEA. The column 1 is operated at a reflux ratio of about 10 to 20. The product obtained at the bottom of the column 1 at a temperature of 260 to 270° C. contains about 93-95% of VEA.

The bottom take-off of the column 1 having a VEA content of about 93 to 95% is then added at a temperature between 180 and 250° C. as feed approximately in the middle of the rectification column 19 having a packing height of 6 to 8 m of the Sulzer Optiflow C36 type. The pressure at the top of the column 19 is about 0.5 to 1 mbar. At the top of the column 19, about 5 to 15% by mass of the feed stream are removed as a top take-off having a content of about 92 to 95% of VEA. The column 19 is operated at a reflux ratio of about 15 to 30. The side take-off point is about 2 to 3 m of packing height below the feed inflow point. At the side take-off, depending on the desired amount of PG, between 40 and 60% (the latter corresponds to 60% of the VEA used in the form of PG) of the feed stream with a VEA content of more than 97% are removed. The desired flow rate is established by regulation of the partial condenser forward flow temperature. The product obtained at the bottom of the column 19 at a temperature of 260 to 270° C. still contains about 82-87% of VEA, depending on the split ratio set.

The bottom product of the columns 19 is now fed to the short-path evaporator 13, which is operated at a pressure of about 0.1 to 0.2 mbar. The residue still contains about 2-5% of VEA, while the VEA content in the distillate is about 92 to 95%, depending on the split. The distillate is mixed together with the top take-off of the column 19 to give VEA TG.

The invention claimed is:

1. Process for the working-up of vitamin E acetate comprising,
    conducting a first purification stage by feeding a product stream to a first rectification column, taking off low-boiling products and unspecified isomers of vitamin E acetate from a top of the first rectification column, and taking off a stream containing vitamin E acetate in purified form at a side and/or a bottom of the first rectification column, and
    conducting a second purification stage by feeding to a second rectification column the stream containing the vitamin E acetate in purified form taken off the side and/or bottom of the first rectification column and removing from the second rectification column one vitamin E acetate stream with a purity of >97% by weight and a further vitamin E acetate stream with a purity of >92% by weight.

2. Process according to claim 1, wherein the vitamin E acetate is removed from the second rectification column as a bottom take-off stream with a purity of >97% by weight and as a top take-off stream with a purity of >92% by weight.

3. Process according to claim 1, wherein the side take-off or the bottom take-off of the first rectification column is fed in the second purification stage to a second rectification column, and wherein the vitamin E acetate is removed from the second rectification column as a side take-off with a purity of >97% by weight and as a mixture consisting of top take-off and distillate of the bottom take-off with a purity of >92% by weight.

4. Process according to claim 2, wherein the bottom take-off of the second column is distilled before it is mixed with the top take-off of the same column.

5. Process according to claim 2, further comprising degassing the product stream in a falling-film evaporator and then adding the degassed product stream to the first rectification column.

6. Process according to claim 2, wherein the side take-off of the first rectification column is passed into the second rectification column, and wherein the process further comprises mixing the bottom take-offs of both the first and second rectification columns with one another and distilling the mixed bottom take-offs, wherein the distilled mixed bottom take-offs together with the top take-off of the second rectification column, form the further stream of vitamin E acetate having a purity of >92% by weight.

7. Process according to claim 2, which comprises conducting distillation in a short-path evaporator.

8. Process according to claim 1, wherein the side take-off is effected by partial condensation of the vapour phase ascending in the first and second rectification columns and wherein a laterally emerging product stream is removed as vapour condensate from the column.

9. Process according to claim 8, wherein the vapour condensate has a purity of >97% by weight.

* * * * *